United States Patent [19]
Garman et al.

[11] Patent Number: 5,893,713
[45] Date of Patent: Apr. 13, 1999

[54] DENTAL PROBE HAVING SUPERELASTIC PLUGGER ELEMENT AND METHOD OF USE THEREOF

[75] Inventors: Gary Garman, La Verne; Eric Shirley, Orange, both of Calif.

[73] Assignee: Kerr Manufacturing Company, Romulus, Mich.

[21] Appl. No.: 08/984,782

[22] Filed: Dec. 4, 1997

[51] Int. Cl.[6] .................... A61C 3/00; A61C 5/02
[52] U.S. Cl. ........................... 433/32; 433/224
[58] Field of Search ............... 433/32, 72, 102, 433/224

[56] References Cited

U.S. PATENT DOCUMENTS

| | | |
|---|---|---|
| 4,527,560 | 7/1985 | Masreliez ............... 128/303.1 |
| 5,043,560 | 8/1991 | Masreliez ............... 219/497 |
| 5,605,460 | 2/1997 | Heath et al. ............. 433/224 |
| 5,752,825 | 5/1998 | Buchanan ................ 433/32 |

*Primary Examiner*—Cary E. O'Connor
*Attorney, Agent, or Firm*—Wood, Herron & Evans L.L.P.

[57] ABSTRACT

A medical or dental probe having a resistive, integrally heated tip including a superelastic material such as nickel-titanium alloy. The probe tip provides a nearly continuous, controllable heat, and it may have a narrow, pointed shape. The tip may be heated rapidly, and it provides rapid heating of the instrument, continuous supply of heat for the purpose desired, and concentration of maximum heat at the end of the tip. The added flexibility allows the tip to follow the curvature of a canal of a tooth without the need to pre-bend the tip which increases the working life of the tip and provides for improved packing of the material used to fill the root canal.

30 Claims, 3 Drawing Sheets

DENTAL PROBE HAVING SUPERELASTIC PLUGGER ELEMENT AND METHOD OF USE THEREOF

FIELD OF THE INVENTION

The present invention generally relates to heated dental probes and, more specifically, to probes having thin tap elements used to pack filler material, such as gutta-percha, into root canals.

BACKGROUND OF THE INVENTION

In dentistry, probes having narrow, heated elements are used in root canal therapy for plugging a previously hollowed root system with heat-softened gutta-percha (natural rubber) or other substances. These heated elements are known as plugger elements or plugger tips and typically comprise plastically deformable stainless steel needle shaped members.

Methods and apparatus for heating these plugger elements are disclosed in U.S. Pat. Nos. 4,527,560 and 5,043,560, each issued to Masreliez, and the disclosures of which are hereby incorporated herein by reference. The heated plugger elements disclosed in the Masreliez patents are very thin and formed of stainless steel. Therefore, they are bendable to hold various shapes, but they are not significantly resilient or elastic.

The permanent deformability of conventional heated plugger elements requires the operator, such as an endodontist, to prebend the elements in an attempt to follow a curved root canal. However, it is very difficult to precisely conform the plugger element to the curvature of the canal in any particular case since the curvature must be approximated, for example, from an X-ray image. Moreover, even if bent in a relatively accurate manner, the permanent bend of the tip tends to make following the root canal difficult or impossible during the root canal procedure. This is especially true when the root canals have a compound curve or a curve with an increasing or decreasing radius. This results in inconsistent packing and shaping of the gutta-percha. Further, it is difficult to straighten the short, rigid plugger elements for reuse.

Another problem area not adequately addressed by prior plugger elements relates to the ability to twist the element during a root canal procedure. The ability to twist the plugger element during the procedure eases the release of the gutta-percha within the root canal. In this regard, in a typical procedure the root canal is filled with gutta-percha and a plugger element is inserted into the gutta-percha to force it into the lateral canals of the root. As the plugger element is inserted within a main canal of the root, the gutta-percha will be forced downward by the end of the plugger element and outward by the outer surface of the plugger element. This latter action forces gutta-percha material into the lateral canals. Twisting of the plugger element has then been used to break the frictional grip between the outer or side surface of the plugger element and the gutta-percha before the plugger element is pulled from the main canal. Rigid plugger elements having a present curvature cannot be adequately twisted by the dentist while they are within a curved main canal. Since these conventional plugger elements cannot be twisted to release the gutta-percha, most of the gutta-percha which is not forced into the lateral canals remains on the plugger element when it is removed from the root canal. The main canal must then be carefully refilled with gutta-percha.

To alleviate problems such as these in the prior art, it would be desirable to provide a temperature controlled dental probe having a reusable plugger element that conforms easily and precisely to root canals regardless of their curvature, and allows for easy release of filler material within the root canals.

SUMMARY OF THE INVENTION

To solve problems specific to tooth packing procedures, therefore, the present invention provides dental probe apparatus including a heated plugger element at least partially formed from a superelastic material. This superelastic plugger element is an elongate, needle shaped member that can follow a convoluted root canal to provide consistent, dense packing of the root canal. The elasticity and resilience of the plugger element also allows it to be twisted within a curved root canal to release filler material adhered to the plugger element. The superelastic plugger element also serves as a resistance heater which allows for controlled, rapid and continuous heating of the filler material. In this regard, the preferred superelastic material is an electrically conductive, nickel-titanium alloy. The invention further contemplates a replaceable and reusable plugger tip including the unique plugger element of the invention.

Other advantages of the invention will become more apparent to those of ordinary skill upon review of the following detailed description of the preferred embodiments taken in conjunction with the accompanying drawings.

DETAILED DESCRIPTION OF THE EMBODIMENTS

Figure 1:
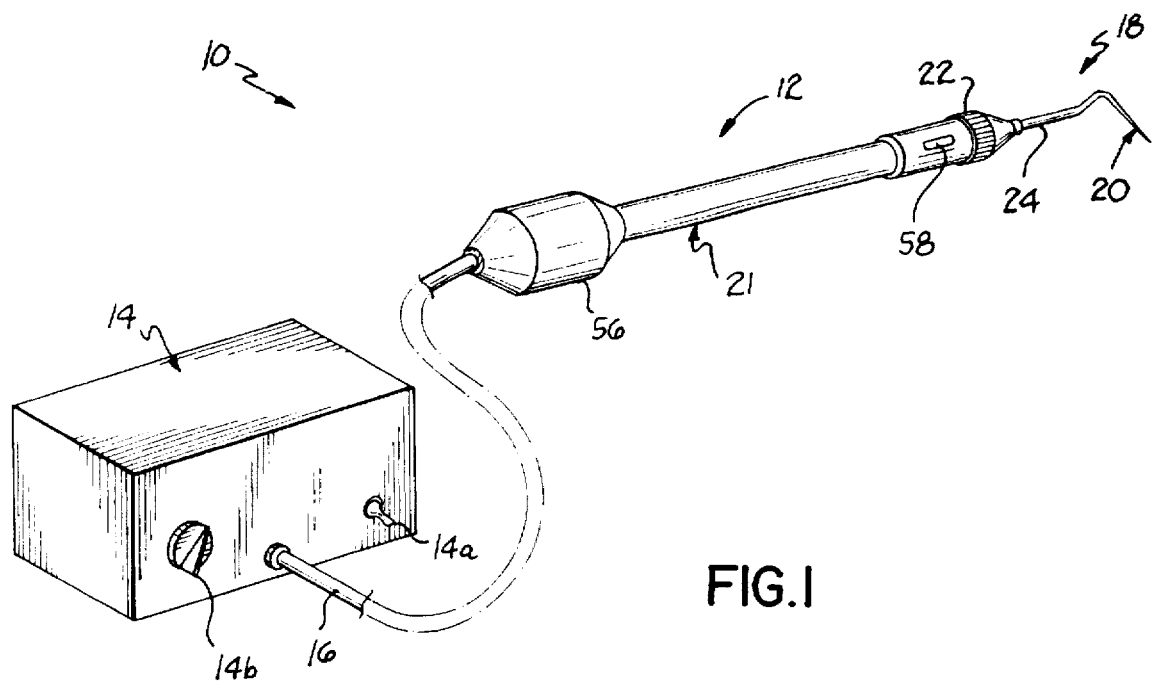
FIG. 1 is a perspective view of an apparatus incorporating a preferred embodiment of the inventive dental probe and superelastic plugger element.

Referring first to FIG. 1, an apparatus 10 is shown and generally includes a temperature controllable probe 12 connected to a conventional control box 14 by a suitable power lead or cord 16. Control box 14 includes a typical on/off switch 14a and a power adjustment dial 14b. The specific controls associated with apparatus 10 and, specifically, control box 14, are generally known by those of skill in the art and may take the form of the control components shown and described in the above incorporated U.S. Pat. No. 4,527,560. As the controls do not form a basis for the present invention, a general description thereof as related to the operation of probe 12 will suffice. Of course, other means for temperature control of probe 12 may be used as well.

Figure 2:
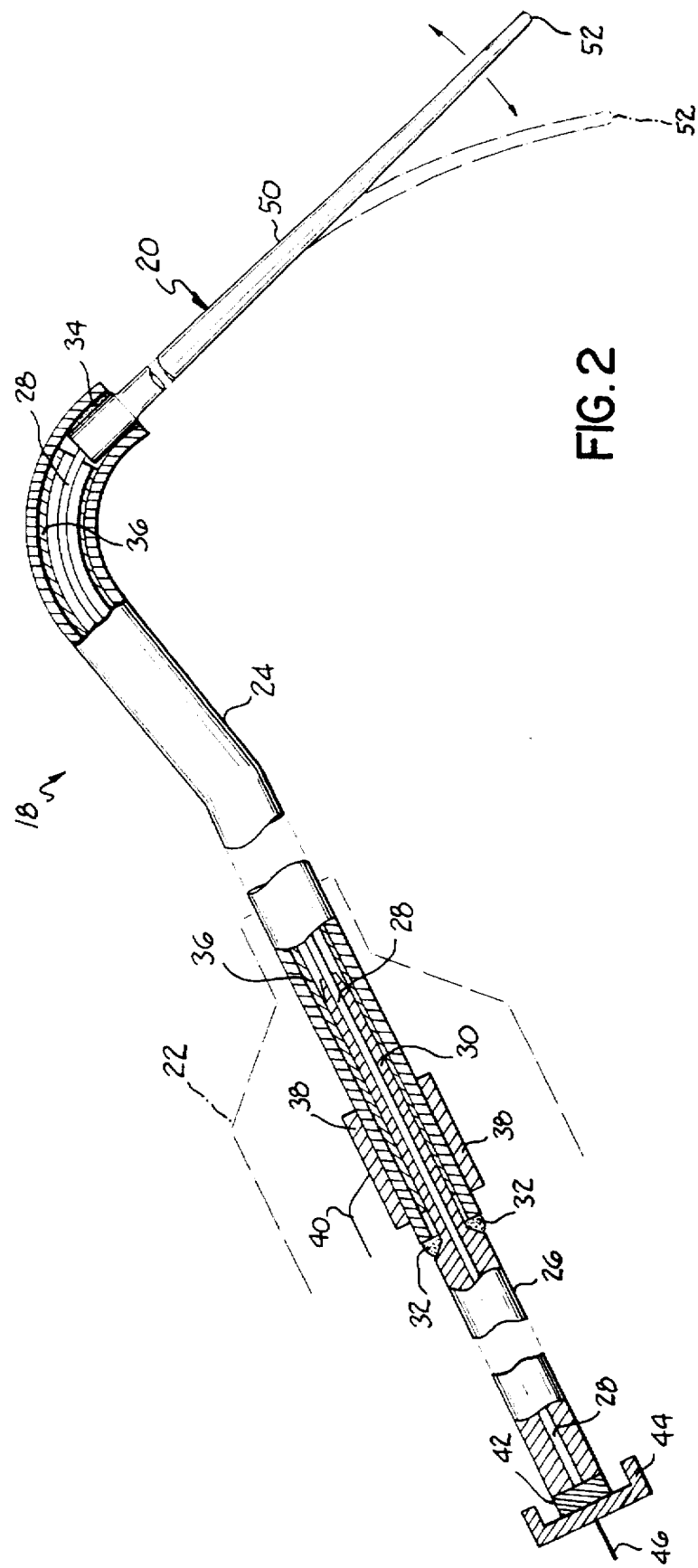
FIG. 2 is a plan view of the replaceable tip portion of the dental probe, partially cut away to show various internal details.

As generally shown in FIG. 1, and more specifically illustrated in FIG. 2, the present invention contemplates a replaceable and reusable plugger tip 18 including an elongate or slender superelastic plugger element 20 in accordance with the invention. Plugger tip 18 may be selectively attached to a handle portion 21 (FIG. 1) of probe 12 by a rotating connection collar 22 as known from the device disclosed in U.S. Pat. No. 4,527,560. As specifically shown in FIG. 2, probe 12 includes a conductive, tubular plugger support element 24 receiving an anchor element 26 at one end. Plugger support element 24 is preferably formed from stainless steel. Anchor element 26 may also be formed of stainless steel but does not function to conduct electrical current. An insulated wire 28 is disposed within anchor element 26 and runs through plugger support element 24 and into plugger element 20 for reasons and in a manner to be described. Anchor element 26 includes a reduced diameter portion 30 inserted within plugger support element 24 and further affixed thereto by a nonconductive epoxy adhesive 32 that prevents electrical conduction between plugger support element 24 and anchor 26. Superelastic plugger element 20 is affixed into the opposite end of plugger support element 24 by solder 34 to allow electrical conduction between plugger element 20 and plugger support element 24 in a manner to be described. An insulative sleeve 36 is disposed within tubular plugger support element 24, as shown in FIG. 2, and receives reduced diameter portion 30 of anchor 26 with a friction fit. Insulative sleeve 36 may be formed of polytetrafluoroethylene (PTFE) to further guard against electrical conduction between insulated wire 28 and tubular plugger support element 24.

As further shown in FIG. 2, an electrically conductive collar 38 is securely affixed to the outside of plugger support element 24 to allow electrical conduction between these two elements. A suitable silver solder (not shown) may be used to facilitate this connection. A first transformer lead 40, schematically shown in FIG. 2, is electrically connected to collar 38. A contact element 42 is electrically connected to wire 28 and physically connected to an end of anchor 26. A second contact element 44 fixed within probe 12 and having a second transformer lead 46 (schematically shown in FIG. 2) contacts element 42 when probe 12 is properly fixed to handle 21 (FIG. 1) through the use of collar 22.

Figure 3:
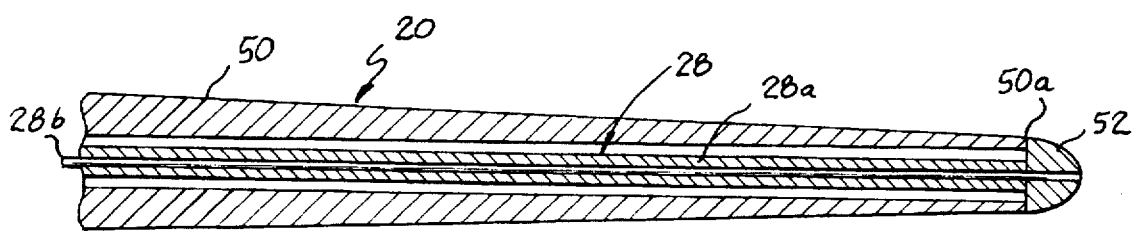
FIGS. 3 and 3A are longitudinal cross-sectional views showing two alternative embodiments of the superelastic plugger element.

Referring now to FIG. 3, the superelastic plugger element 20 of the present invention includes an outer, needle shaped member 50 formed from a superelastic alloy. Plugger element 20 also includes a portion of insulated wire 28, and a suitable electrically conductive tip element 52. Needle shaped member 50 may be ground to have a tapered outer surface. The interior of member 50 is hollow to receive wire 28. As shown in FIG. 3, tip element 52 may be slightly rounded and may simply comprise a silver solder. In the embodiment shown in FIG. 3, wire 28 has been stripped of insulation 28a at an end thereof surrounded by conductive tip element 52. Therefore, solder 52 makes electrical contact with exposed wire 28b and with needle shaped member 50. Superelastic needle shaped member 50 is therefore electrically isolated and disconnected from wire 28 except at a distal end 50a contacting solder 52.

Figure 3A:
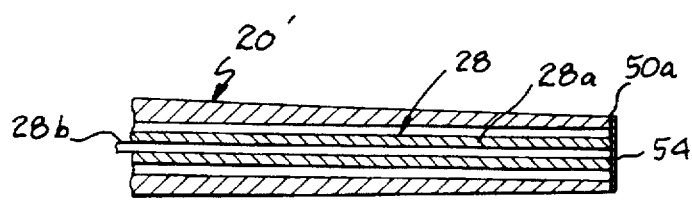

An alternative end construction is shown in FIG. 3A with reference to a plugger element 20'. In this alternative embodiment, wire 28 and, specifically, internal wire 28b is simply welded or brazed to needle shaped member 50 by a suitable, electrically conductive welding or brazing compound 54 which will conduct electrical current between wire 28b and needle shaped superelastic member 50. Therefore, with regard to both embodiments of plugger element 20 and 20', electrical current is carried through wire 28b to distal end 50a, where the current will pass through either solder 52 or brazing or welding compound 54 and into superelastic needle shaped member 50. This will heat distal end 50a in a manner to be described more completely below.

Outer needle shaped member 50 may be formed from various electrically conductive superelastic alloys. These include alloys such as nickel-titanium (NiTi) that may withstand several times more strain than conventional materials, such as stainless steel, without significant plastic deformation. A superelastic material will generally recover approximately 6% after deformation at ambient temperature while stainless steel will recover only 1–2% after deformation. Typically, superelastic alloys undergo a stress induced martensitic transformation which allows for shape memory properties. Shape memory and superelasticity are found in stoichiometric NiTi, near-equiatomic Ni—Ti, for example, 50.8 atomic percent Ti and 49.2 atomic percent Ni, Ni—Ti—Cu, Ni—Ti—Nb and Ni—Ti—Fe alloys as well as beta-phase titanium or other Ti based alloys. Examples of suitable nickel-titanium alloys in various stoichiometric ratios are disclosed in U.S. Pat. No. 5,044,947 (nickel-titanium-copper alloy) and U.S. patent applications Ser. Nos. 08/221,638 and 08/454,016, of Sachdeva et al., entitled "NiTiNb Alloy Processing Method and Articles Formed Thereby" (nickel-titanium-niobium-alloy). The disclosures of U.S. Pat. No. 5,044,947 and the aforesaid applications are hereby incorporated in their entirety by reference herein.

The specific superelastic alloy composition is not critical to the present invention. Other materials which exhibit superelastic properties may be used as well. For example U.S. Pat. No. 5,429,501, hereby incorporated by reference herein, discloses superelastic and shape memory beta-phase titanium. To form beta-phase titanium, metallic titanium may be alloyed with molybdenum, chromium, zirconium, tin, vanadium, iron or niobium. Other compositions such as Cu—Zn alloys are also known to be superelastic and are suitable for use in the present invention. Another material suitable for use in the present invention is a work hardened nickel titanium having a martensitic crystal structure, such as that sold under the trademark NITANOL for orthodontic wires by Unitek Corp. of Arcadia, Calif.

From the foregoing description of FIG. 2, and as generally known from the device described in the above incorporated U.S. Pat. No. 4,527,560, the operation of probe 12 to heat plugger element 20 will be understood. Referring to FIGS. 1 and 2, the replaceable and reusable plugger tip 18, which generally includes plugger element 20, support element 24, and collar 22, is connected to handle 21. Handle 21 is electrically insulated to allow it to be gripped by the endodontist. The proximal end of probe 12 includes a conventional step down transformer 56 having one winding (not shown) electrically connected with wire 28 through lead 46 and contacts 42 and 44, as shown in FIG. 2, and another winding (not shown) electrically connected to plugger support element 24 through lead 40 and sleeve 38 as previously described. As known, the use of a transformer 56 within probe 12 allows the relatively high voltage and low current supplied through control box 14 to be stepped down to a relatively low voltage and higher current within probe 12 and through to plugger element 20. It will be appreciated that control box 14 is normally supplied with power from a standard 115V wall outlet. The voltage and current requirements of plugger element 20 will vary based upon size and desired temperature, however, 5–20 watts of power are typically supplied to plugger element 20 to heat distal end 50a to an optimal temperature of between 200° C.–300° C. This will be above the softening temperature of a typical filler material, such as natural gutta percha rubber. A push button 58 may be incorporated into handle 21 of probe 12 as a switch to supply electrical current to plugger element 20 (FIG. 1). A suitable touch control sensor is shown and described in U.S. Pat. No. 4,177,799, the disclosure of which is hereby incorporated by reference herein.

In order to heat plugger element 20, current is supplied from transformer 56 via respective leads 40, 46 to conductive tubular plugger support element 24 and wire 28 respectively via contacts 38 and 42. Electrical current is then supplied to needle shaped superelastic member 50 from support element 24 via soldered connected 34 and to distal end 50a through wire 28b via soldered connection 52 or a brazed or welded connection 54 (FIGS. 3 and 3A). As shown in FIGS. 3 and 3A, the cross sectional area of needle shaped superelastic member 50 increases as the distance away from distal end 50a increases. As needle shaped superelastic member 50 has an electrical resistance greater than that of wire 28b, needle shaped member 50 forms a resistance heater. The distal taper provides an increased current density at distal end 50a and therefore heats distal end 50a as well as solder 52 or brazing or welding compound 54 to a higher temperature than that of more proximal portions of superelastic needle shaped member 50.

Figure 4:
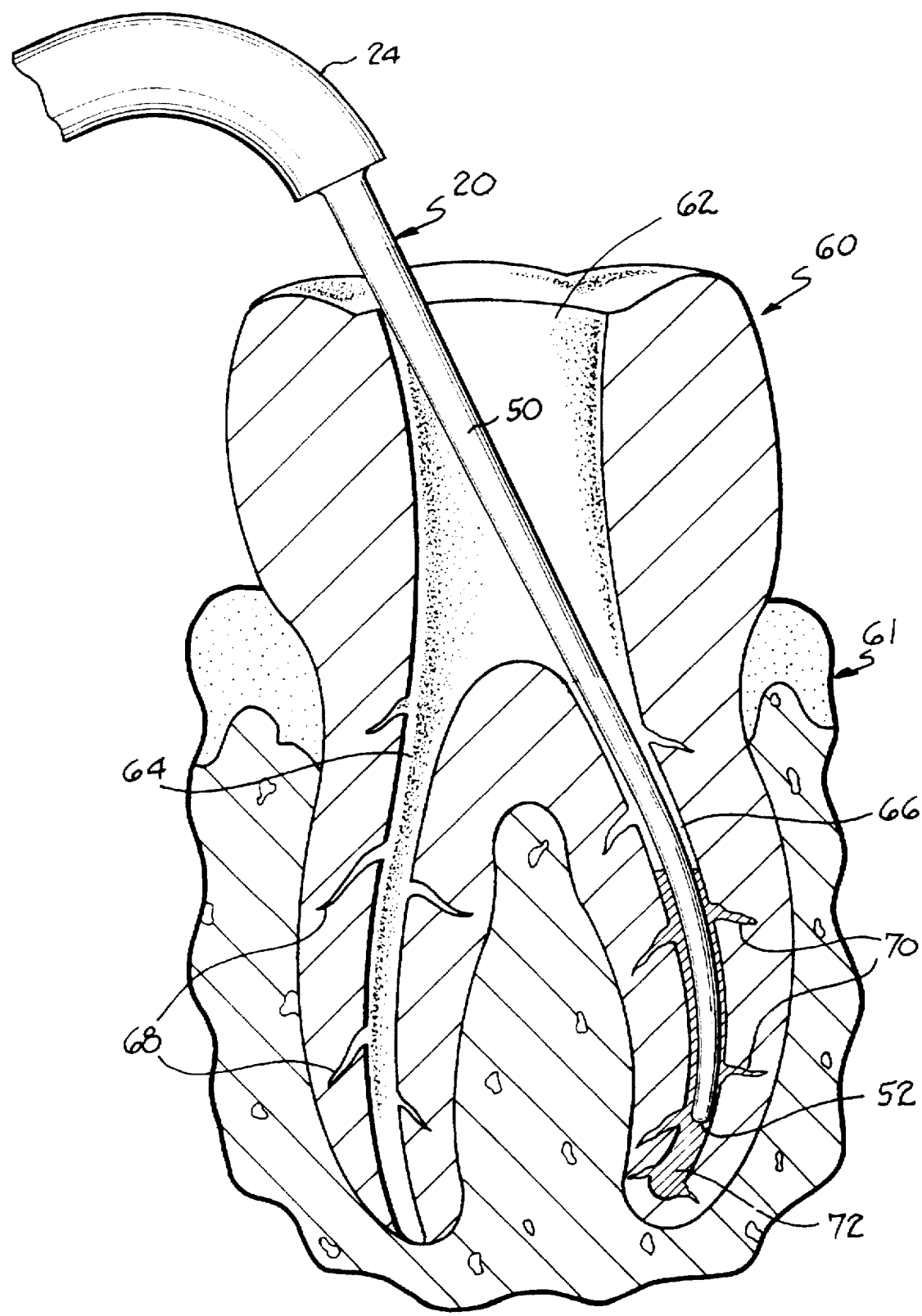
FIG. 4 is a cross-sectional view of a tooth showing the superelastic plugger element of the present invention used during a root canal packing procedure.

FIG. 4 illustrates molar 60 contained in a lower jaw 61 and undergoing a root canal procedure with the inventive superelastic plugger element 20. Tooth 60 is initially prepared by removing decayed material from a root canal 62. Root canal 62 includes main canals 64, 66 as well as lateral canals 68, 70 extending from each main canal 64, 66. During a typical root canal procedure, main canals 64, 66 are packed with a filler material 72, such as gutta percha rubber. Plugger element 20 is heated in the above described manner and filler material 72 is placed within canal 62 and, more specifically, down into one of the main root canals 66. Heated plugger element 20 is used to soften and force filler material 72 tightly within canal 66 by movement of plugger element 20 up and down within the canal 66. For curved root canals, as shown, it is important that the plugger element 20 follow the curvature. Superelastic plugger element 20 will elastically or resiliently follow any curvature, including compound curvatures, by curving or straightening, as appropriate, as the plugger element 20 is reciprocated up and down within canal 66 by the endodontist.

After main root canal 66 is partially filled, plugger element 20 is forced down into the filler material 72 and this forces filler material 72 into lateral canals 70. Plugger element 20 may then be broken free from filler material 72 by twisting plugger element 20 about its longitudinal axis. Due to the superelastic nature of plugger element 20, this twisting action may be performed even with the plugger element 20 contained in and following a curved canal 66 as shown in FIG. 4. Without this twisting motion, a substantial amount of filler material 72 in main root canal 66 may adhere to plugger element 20 as plugger element 20 is removed from tooth 60. This aspect of the invention simplifies the packing procedure of canal 62 and provides for dense packing of filler material 72 without voids.

While preferred plugger elements 20 and 20' have been described along with their methods of construction, those skilled in the art will readily recognize modifications that may be made to the embodiments disclosed. These modifications are intended to be a part of the invention if they use the underlying concepts of this invention. The claims of this invention should be interpreted to the extent allowable by reference to this description and to the prior art. The preferred embodiments disclosed should be used only to the extent necessary to define the invention. Specifically, the superelastic needle shaped member 50 may be of uniform cross-sectional area if heat concentration at distal end 50a is not desired. Also, distal end 50a may generally assume a variety of shapes other than the shape shown herein. For example, end 50a may be flattened to a trowel-like configuration or the flattened end may further be formed into a spoon.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method as shown and described. This has been a description of the present invention, along with the preferred method of practicing the present invention as currently known. However, the invention itself should only be defined by the appended claims.

What is claimed is:

1. A temperature controllable apparatus for performing root canal packing procedures, the apparatus comprising:

an electrical power control; and a probe electrically connected to the power control and including a handle operatively connected to an elongate superelastic plugger element, the superelastic plugger element forming a resistance heater receiving electrical current from the power control and having at least a portion thereof formed of superelastic material;

whereby an operator may insert the superelastic plugger element into a curved root canal while the superelastic plugger element resiliently follows the curvature of the root canal and the operator may twist the superelastic plugger element within the curved root canal upon removal thereof to help prevent removing filler material from the root canal.

2. The apparatus of claim 1 wherein the superelastic plugger element is a hollow, needle shaped member receiving an insulated wire.

3. The apparatus of claim 2 wherein the hollow, needle shaped member is formed of a superelastic material.

4. The apparatus of claim 3 wherein the wire and the hollow, needle shaped member are electrically connected at a distal end of the needle shaped member.

5. The apparatus of claim 1 wherein the superelastic plugger element comprises a superelastic material selected from the group consisting of nickel alloys, nickel titanium alloy, near-equiatomic Ni—Ti alloy, Ni—Ti—Nb alloys, Ni—Ti—Fe alloys, Ni—Ti—Cu alloys, Ni—Ti—Nb alloys and beta-phase titanium.

6. The apparatus of claim 5 wherein said superelastic nickel titanium alloy is at least 40% Ti.

7. The apparatus of claim 5 wherein said superelastic nickel titanium alloy is about 55% Ni and about 45% Ti.

8. The apparatus of claim 5 wherein said superelastic nickel titanium alloy is about 55.2% Ni and about 44.8% Ti.

9. The apparatus of claim 1 wherein the superelastic plugger element increases in cross-sectional area in a direction away from a distal end thereof.

10. A dental probe comprising:

a handle;

an elongate superelastic plugger element operatively connected to the handle, the plugger element having at least a portion thereof formed of a superelastic, electrically conductive material wherein the superelastic plugger element is a hollow, needle shaped member receiving an insulated wire to form a resistance heater;

whereby the superelastic plugger element may be electrically heated and an operator may insert the superelastic plugger element into a curved root canal while the superelastic plugger element resiliently follows the curvature of the root canal and the operator may twist the superelastic plugger element within the curved root canal upon removal thereof to help prevent removing filler material from the root canal.

11. The probe of claim 10 wherein the hollow, needle shaped member is formed of a superelastic material.

12. The probe of claim 11 wherein the wire and the hollow, needle shaped member are electrically connected at a distal end of the needle shaped member.

13. The probe of claim 10 wherein the superelastic plugger element comprises a superelastic material selected from the group consisting of nickel alloys, nickel titanium alloy, near-equiatomic Ni—Ti alloy, Ni—Ti—Nb alloys, Ni—Ti—Fe alloys, Ni—Ti—Cu alloys, Ni—Ti—Nb alloys and beta-phase titanium.

14. The probe of claim 13 wherein said superelastic nickel titanium alloy is at least 40% Ti.

15. The probe of claim 13 wherein said superelastic nickel titanium alloy is about 55% Ni and about 45% Ti.

16. The probe of claim 13 wherein said superelastic nickel titanium alloy is about 55.2% Ni and about 44.8% Ti.

17. The probe of claim 10 wherein said plugger element increases in cross-sectional area in a direction away from a distal end thereof.

18. A superelastic, reusable plugger tip comprising:

an elongate superelastic plugger element having proximal and distal ends and at least partially formed from a superelastic, electrically conductive material;

a plugger support element supporting the superelastic plugger element at the proximal end and electrically connected thereto; and an insulated, electrically conductive element disposed within the superelastic plugger element and electrically connected thereto at the distal end;

whereby the superelastic plugger element may be electrically heated and an operator may insert the superelastic plugger element into a curved root canal while the superelastic plugger element resiliently follows the curvature of the root canal and the operator may twist the superelastic plugger element within the curved root canal upon removal thereof to help prevent removing filler material from the root canal.

19. The plugger tip of claim 18 wherein the superelastic plugger element is a hollow, needle shaped member and the insulated, electrically conductive element is an insulated wire.

20. The plugger tip of claim 19 wherein the hollow, needle shaped member is formed of a superelastic material.

21. The plugger tip of claim 18 wherein the superelastic plugger element comprises a superelastic material selected from the group consisting of nickel alloys, nickel titanium alloy, near-equiatomic Ni—Ti alloy, Ni—Ti—Nb alloys, Ni—Ti—Fe alloys, Ni—Ti—Cu alloys, Ni—Ti—Nb alloys and beta-phase titanium.

22. The plugger tip of claim 21 wherein said superelastic nickel titanium alloy is at least 40% Ti.

23. The plugger tip of claim 21 wherein said superelastic nickel titanium alloy is about 55% Ni and about 45% Ti.

24. The plugger tip of claim 21 wherein said superelastic nickel titanium alloy is about 55.2% Ni and about 44.8% Ti.

25. The plugger tip of claim 18 wherein the superelastic plugger element increases in cross-sectional area in a direction away from a distal end thereof.

26. The plugger tip of claim 18 further including a collar disposed around the plugger support element for allowing selective attachment of the plugger tip to a dental probe.

27. A method of filling an endodontically prepared root canal comprising the steps of:

inserting heat-softenable filler material having a specified softening temperature into the root canal;

inserting a superelastic plugger element into the root canal;

heating the plugger element to a temperature exceeding the softening temperature of the filler material; and contacting the filler material with the heated plugger element sufficiently to soften the filler and, while the filler material is softened, urging the plugger element into the root canal against the filler material to densify and pack it into the root canal.

28. The method of claim 27 wherein the root canal is curved and further comprising the step of:

rotating and withdrawing the plugger element from the root canal after densifying and packing the filler material therein.

29. The method of claim 28 wherein the contacting step includes reciprocating the plugger element within the root canal to repeatedly contact the filler material to effect the densification and packing thereof in the root canal.

30. In an apparatus including an electrically heated probe for performing root canal packing procedures, the probe being connected to an electrical power control and including a handle to be gripped by an operator while performing a root canal packing procedure, wherein the improvement comprises:

a superelastic plugger element operatively connected to the handle and forming an electrical resistance heater receiving electrical current from the power control and having at least a portion thereof formed of superelastic material.

* * * * *